(12) United States Patent
El-Dabh (10) Patent No.: US 8,795,292 B1
(45) Date of Patent: Aug. 5, 2014

(54) DEVICE AND METHOD FOR TREATING POST-PARTUM HEMORRHAGE

(76) Inventor: Ashraf El-Dabh, Westlake, OH (US)

( * ) Notice: Subject to any disclaimer, the term of this patent is extended or adjusted under 35 U.S.C. 154(b) by 0 days.

(21) Appl. No.: 13/458,181

(22) Filed: Apr. 27, 2012

Related U.S. Application Data (60) Provisional application No. 61/479,530, filed on Apr. 27, 2011.

(51) Int. Cl.
*A61B 17/42* (2006.01)
*A61B 17/46* (2006.01)

(52) U.S. Cl.
USPC .......................................... 606/119; 606/151

(58) Field of Classification Search
USPC ......... 606/119, 151, 155, 157, 158, 192, 201, 606/202; 604/101.01–101.05, 103, 604/103.03–103.09; 128/836; 601/148, 151
See application file for complete search history.

(56) References Cited

U.S. PATENT DOCUMENTS

| | | | |
|---|---|---|---|
| 5,057,117 A | | 10/1991 | Atweh |
| 6,126,634 A | * | 10/2000 | Bagaoisan et al. ....... 604/101.02 |
| 6,676,680 B1 | | 1/2004 | Packer |
| 7,172,603 B2 | | 2/2007 | Burbank et al. |
| 7,325,546 B2 | | 2/2008 | Burbank et al. |
| 7,404,821 B2 | | 7/2008 | Burbank et al. |
| 2004/0158264 A1 | * | 8/2004 | Adams et al. ................. 606/139 |
| 2012/0172898 A1 | * | 7/2012 | Pedrick et al. ............... 606/151 |

FOREIGN PATENT DOCUMENTS

| | | |
|---|---|---|
| WO | WO 2009/103298 A2 | 8/2009 |
| WO | WO 2009/103298 A3 | 8/2009 |
| WO | WO 2009/103298 A4 | 8/2009 |

* cited by examiner

*Primary Examiner* — Katherine M Shi
(74) *Attorney, Agent, or Firm* — Fay Sharpe LLP (57) ABSTRACT

A post-partum hemorrhage treatment device includes an anterior wall, a posterior wall, and a flexible joint that connects the anterior and posterior walls. The anterior and/or posterior wall includes an inflation chamber that is adapted for selective inflation. A left stud fastener and a left stud-receiving aperture are both located on a left lateral side of the device. A right stud fastener and a right stud-receiving aperture are both located on a right lateral side of the device. The left and right stud fasteners are selectively inserted into and retained in the left and right stud-receiving apertures, respectively, for securing the treatment device relative to a human uterus. A fluid is communicated into the inflation chamber to urge the anterior and posterior surfaces of the uterus toward each other. The stud fasteners are inflatable so as to be secured in their respective stud-receiving apertures.

6 Claims, 8 Drawing Sheets

FIG. 3
(FRONT)

FIG. 4
(SIDE)

FIG. 5
(REAR)

DEVICE AND METHOD FOR TREATING POST-PARTUM HEMORRHAGE

CROSS-REFERENCE TO RELATED APPLICATION

This application claims priority from and benefit of the filing date of U.S. provisional patent application Ser. No. 61/479,530 filed Apr. 27, 2011, the entire disclosure of which is hereby expressly incorporated by reference into the present specification.

BACKGROUND

Post-partum hemorrhage is a leading cause of maternal morbidity and mortality worldwide and is also a leading cause for maternal admission to the intensive care unit (ICU). Uterine atony is the primary cause of post-partum hemorrhage due to the inability of the uterine muscles to contract sufficiently to compress and constrict the internal blood vessels following delivery of a baby.

Intrauterine balloons and other intrauterine devices for treatment of post-partum hemorrhage have been found to be sub-optimal in many cases. In other procedures, sutures are placed in the outer surfaces of the uterine walls to compress the anterior and posterior walls of the uterus together to stop the bleeding. These sutures must be placed by a skilled surgeon in a limited time window, which is often not possible. Although helpful in many cases, these sutures have the following shortcomings:
1—Can be technically difficult to place
2—May result in injury of the Fallopian tubes, ureters or both
3—No tension gauge adjustment is possible. Excessive tension has been reported to cause necrosis of the uterine muscle.
4—Stay permanently in the body; resulting in adhesions between the uterus and the surrounding organs, particularly the bowel
5—Infected blood collections inside the uterus may result in pockets of infection.

This has been reported to create adhesions inside the uterine cavity or severe infections necessitating a hysterectomy.

Accordingly, a need has been identified for a new and improved device and method for treating post-partum hemorrhage.

SUMMARY

In accordance with a first aspect of the present development, a post-partum hemorrhage treatment device includes an anterior wall, a posterior wall, and a flexible joint that connects the anterior wall to the posterior wall. At least one of the anterior wall and the posterior wall includes an inflation chamber that is adapted for selective inflation. A left lateral side of the anterior wall is adapted to be selectively connected to a left lateral side of the posterior wall, and, a right lateral side of the anterior wall is adapted to be selectively connected to the right lateral side of the posterior wall.

In accordance with another aspect of the present development, a post-partum hemorrhage treatment device includes an anterior wall, a posterior wall, and a flexible joint that connects the anterior wall to the posterior wall. At least one of the anterior wall and the posterior wall includes an inflation chamber that is adapted for selective inflation. A left stud fastener and a left stud-receiving aperture are both located on a left lateral side of the device. A right stud fastener and a right stud-receiving aperture are both located on a right lateral side of the device. The left stud fastener is connected to one of the anterior and posterior walls and the left stud-receiving aperture is located in the other of the anterior and posterior walls. The right stud fastener is connected to one of the anterior and posterior walls and the right stud-receiving aperture is located in the other of the anterior and posterior walls. The left and right stud fasteners are selectively inserted into and retained in the left and right stud-receiving apertures, respectively, for securing the treatment device relative to a human uterus.

In accordance with a further aspect of the present development, a post-partum hemorrhage treatment method includes locating an anterior wall of a treatment device adjacent an anterior surface of a uterus and locating a posterior wall of a treatment device adjacent a posterior surface of the uterus. A left lateral side of the anterior wall of the treatment device is connected to a left lateral side of the posterior wall of the treatment device, and a right lateral side of the anterior wall of the treatment device is connected to a right lateral side of the posterior wall of the treatment device. A fluid is communicated into an inflation chamber located in at least one of the anterior and posterior walls of the treatment device to urge the anterior and posterior surfaces of the uterus toward each other.

DETAILED DESCRIPTION

Figure 1:
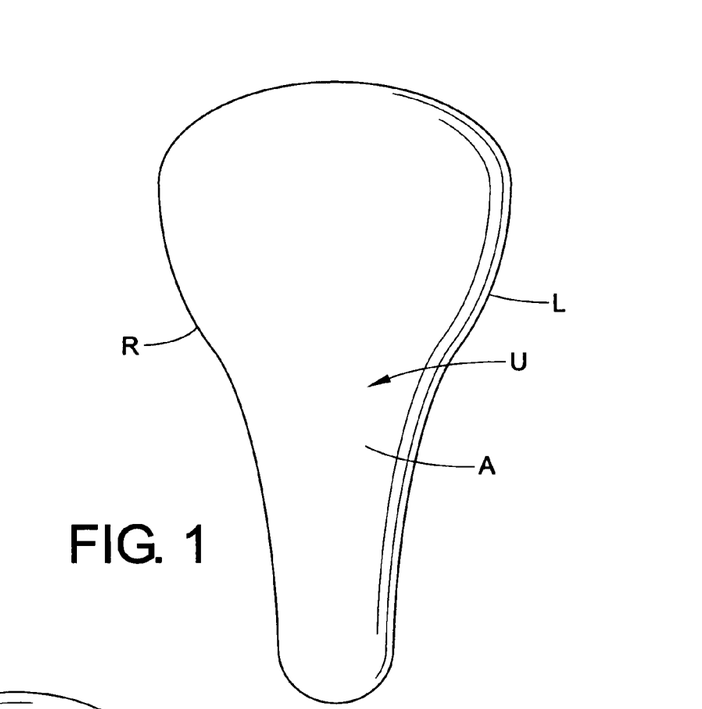
FIG. 1 is a simplified or diagrammatic front view of a human uterus U.
Figure 2:
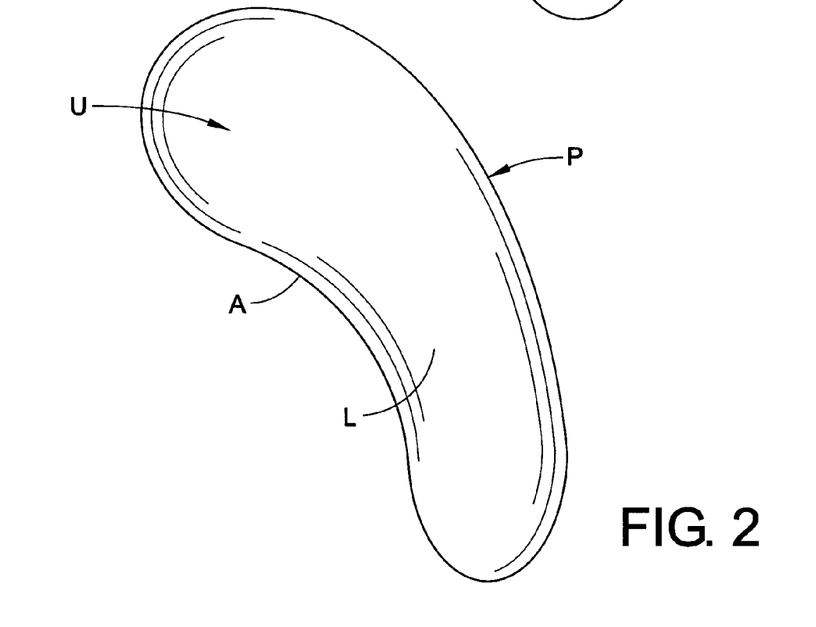
FIG. 2 is a simplified side view of the uterus U shown in FIG. 1.

FIG. 1 is a simplified or diagrammatic front view of a human uterus U, and FIG. 2 is a simplified side view of the uterus U shown in FIG. 1. The uterus comprises an anterior wall or surface A and a posterior wall or surface P, a left lateral side or surface L and a right lateral side or surface R.

Figure 3:
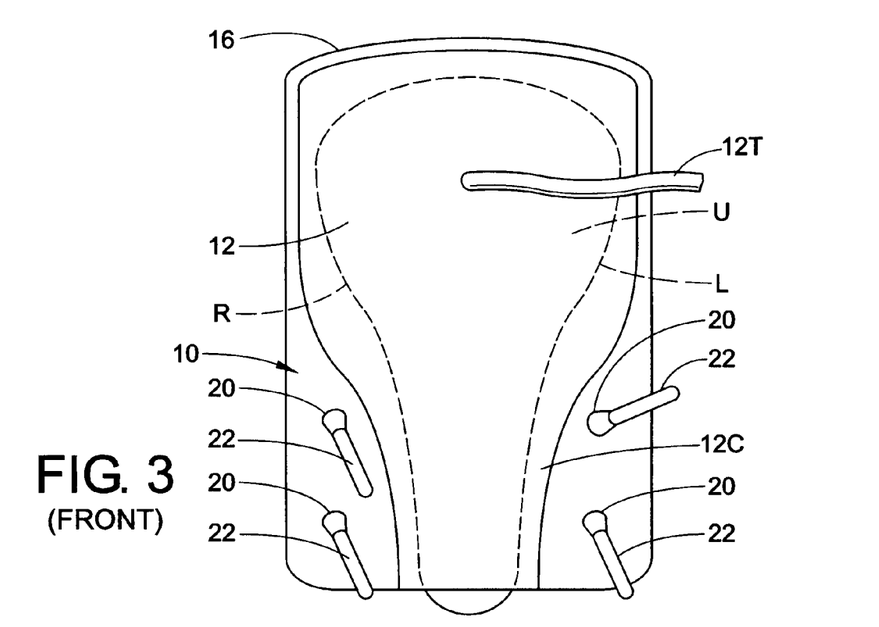
FIGS. 3 and 4 are further front and side views of the uterus U corresponding respectively to FIGS. 1 and 2, but further show a post-partum hemorrhage treatment device 10 formed in accordance with the present development installed on the uterus.
Figure 4:
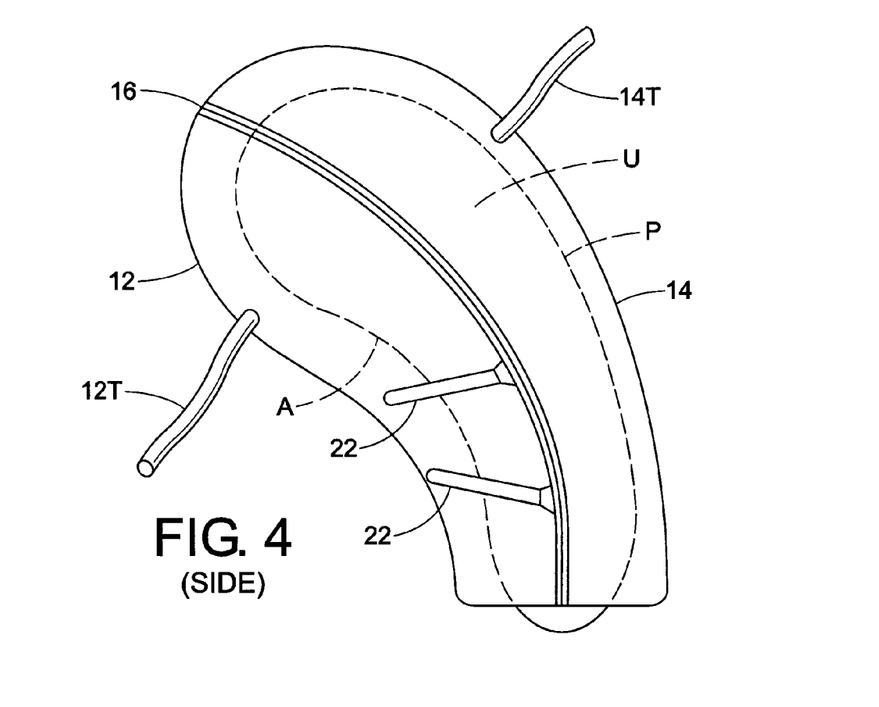
Figure 5:
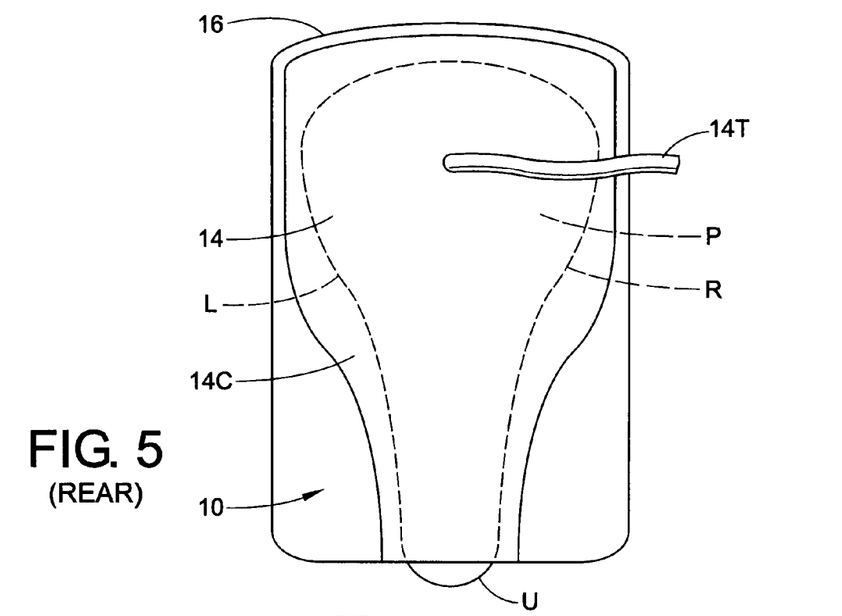
FIG. 5 provides a rear view of the uterus U and the treatment device 10 installed thereon.
Figure 6:
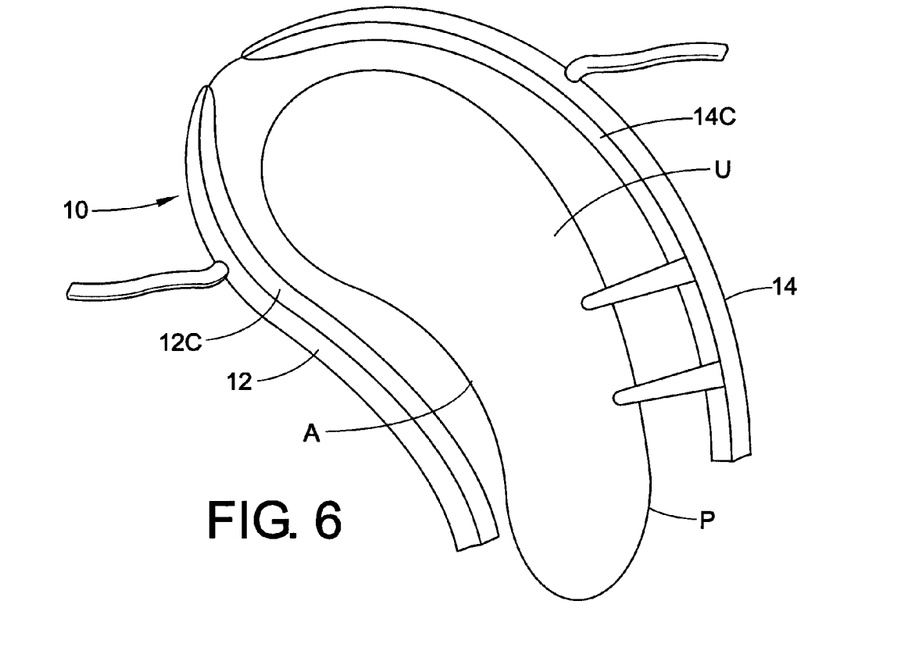
FIG. 6 is a side view that shows the treatment device 10 partially installed on the uterus U.

FIGS. 3 and 4 are further front and side views of the uterus U corresponding respectively to FIGS. 1 and 2, but further show a post-partum hemorrhage treatment device 10 formed in accordance with the present development installed on the uterus U to prevent post-partum hemorrhage due to uterine atony or other causes. FIG. 5 provides a rear view of the uterus U and the treatment device 10 installed thereon. FIG. 6 is a side view that shows the treatment device 10 partially installed on the uterus U.

Figure 7:
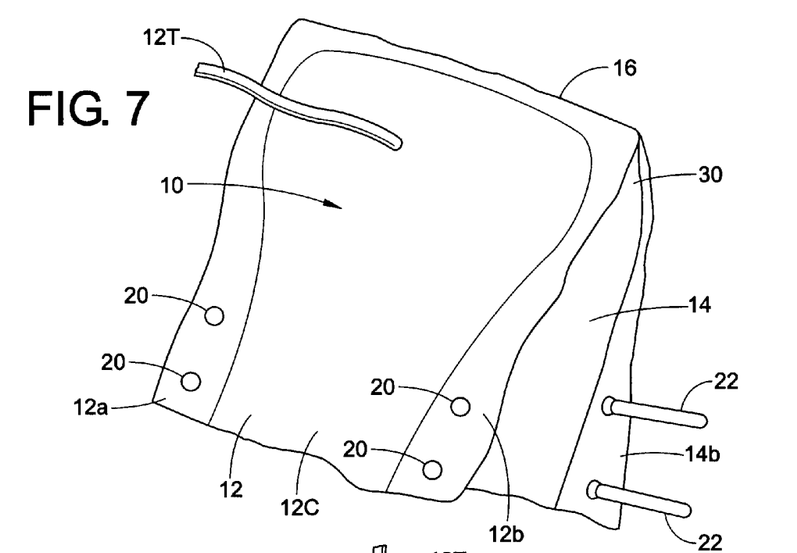
FIGS. 7 and 8 are first and second isometric views of the device 10.
Figure 8:
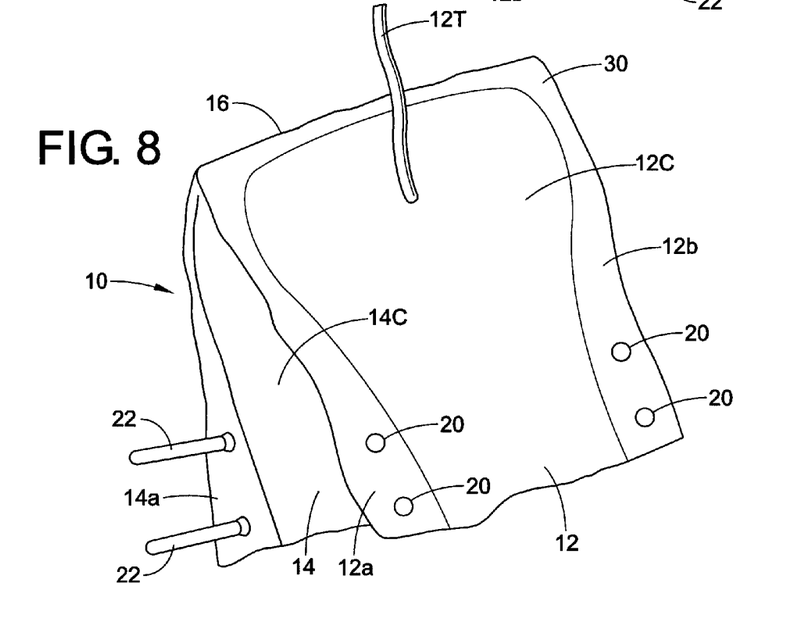
Figure 9:
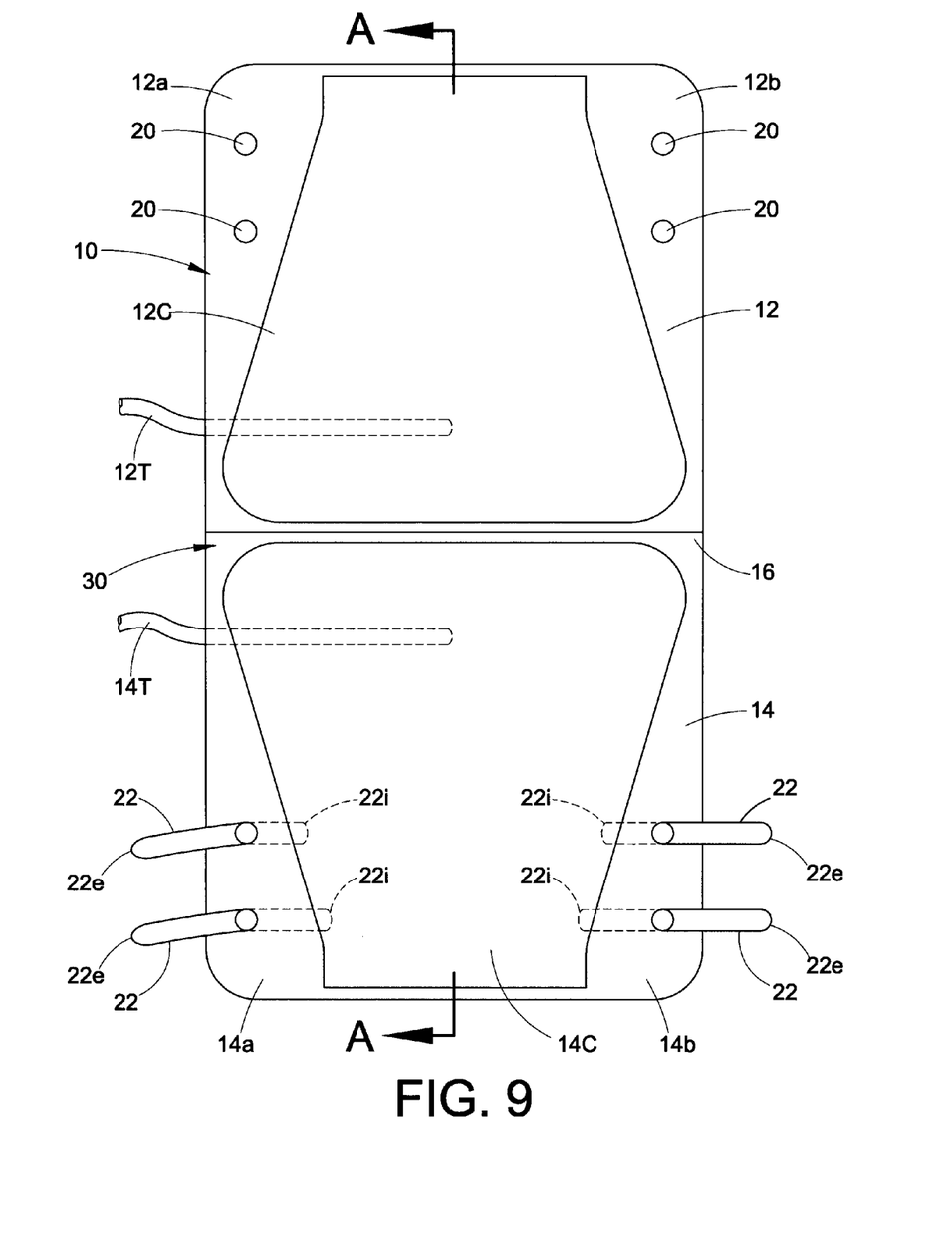
FIG. 9 shows the device 10 in an unfolded or flat state.

FIGS. 7 and 8 are first and second isometric views of the device 10, and FIG. 9 shows the device 10 in an unfolded or flat state.

Referring to all of FIGS. 3-9, it can be seen that the device 10 comprises an anterior wall 12 and a posterior wall 14. The anterior wall 12 is joined or connected to the posterior wall 14 by a flexible main joint or main seam 16. In the exemplary embodiment, the anterior wall 12 and the posterior wall 14 are each defined from a suitable resilient, elastic polymeric material that can be used safely for surgical procedures, such as soft silicone or rubber or other elastomeric or polymeric composition or material, but it is not intended that the device 10 be limited to any particular material.

With reference to FIG. 6, the device 10 is intended to be installed on a human uterus U as shown in FIG. 6, which shows the device 10 in its partially installed state. In FIG. 6, it can be seen that during installation of the device 10, the anterior wall 12 of the device 10 is positioned adjacent and in covering relation with at least part of the anterior wall A of the uterus U, and the posterior wall 14 of the device 10 is positioned adjacent and in covering relation with at least part of the posterior wall P of the uterus U. As shown in FIGS. 7-9, the device 10 includes a left lateral side as defined by the left lateral sides 12*a*,14*a* of the anterior and posterior walls 12,14, and the device 10 includes a right lateral side as defined by the right lateral sides 12*b*,14*b* of the anterior and posterior walls 12,14.

To secure the device 10 in its operative position relative to the uterus U as shown in FIGS. 3-5, the anterior wall 12 and the posterior wall 14 of the device 10 are secured to each other adjacent the left and right sides L,R of the uterus U such that the uterus U is located between and in contact with the device walls 12,14 such that the uterine walls A,P are compressed between the device walls 12,14 to stop bleeding inside the uterus. In particular, the left side 12*a* of the anterior wall 12 is releasably secured to the left side 14*a* of the posterior wall 14, and the right side 12*b* of the anterior wall 12 is releasably secured to the right side 14*b* of the posterior wall 14. In the illustrated embodiment, the left and right sides 12*a*,12*b* of the anterior wall 12 each include at least one stud-receiving aperture 20, i.e., one or more left stud-receiving apertures on the left side 12*a* and one or more right stud-receiving apertures on the right side 12*b*. As shown, the left and right sides 12*a*,12*b* each include first and second stud-receiving apertures 20. Correspondingly, the left and right sides 14*a*,14*b* of the posterior wall 14 each includes at least one projecting fastener stud 22 projecting outwardly therefrom, i.e., one or more left fastener studs 22 on the left side 14*a* and one or more right fastener studs 22 on the right side 14*b*. As shown, the left and right sides 14*a*,14*b* each include first and second fastener studs 22. Preferably, an outer end of each stud 22 is more compliant than the body of the stud and/or is conformed to have a balloon like structure. This will result in the outer tip inflating like a balloon to be larger than the remainder of the stud 22 when the posterior chamber/compartment 14C of the device 10 is inflated. Once inflated, the studs 22 will be retained in a corresponding stud-receiving aperture 20 as long as the posterior chamber/compartment 14C is inflated. The enlarged balloon tip of each stud 22 will further ensure that each stud 22 cannot be withdrawn from the corresponding stud-receiving aperture 20 through which it has been inserted until the stud 22 is deflated. At least one corresponding stud-receiving aperture 20 is provided for and located to receive each respective fastener stud 22.

As shown in FIGS. 3 and 4, the each fastener stud 22 is inserted through a corresponding stud-receiving aperture 20, and the fastener stud 22 is pulled fully through the aperture 20 to draw the anterior and posterior walls 12,14 of the device 10 together. The studs 22 are frictionally or otherwise secured in their respective apertures 20 and are releasable therefrom by deflating the posterior compartment 14C of the device 10 as described in more detail below. In the exemplary embodiment, as described in more detail below, the fastener studs 22 are selectively inflatable such that they expand and become radially enlarged and frictionally engaged in their respective apertures 20 when inflated, but are easily disengaged from in their respective apertures 20 when deflated. Of course, some or all of the fastener studs 22 can be connected to the anterior wall 12 instead of the posterior wall 14, in which case the corresponding stud-receiving aperture 20 is relocated to the posterior wall 14 in order to mate with the fastener stud 22. In one embodiment, the device 10 includes one or more left fastener studs 22 on its left lateral side and one or more right fastener studs on its right lateral side. For both the first (left) studs/apertures 22/20 and the second (right) studs/apertures 22/20, the one or more studs 22 are connected to either the anterior or posterior wall 12,14, and the corresponding one or more stud-receiving apertures 20 are located in the other of the anterior and posterior walls 12,14. Other structures and methods for respectively connecting the left and right sides 12*a*,12*b* of the anterior wall 12 to the left and right sides 14*a*,14*b* of the posterior wall 14 are possible. In one alternative embodiment, the left sides 12*a*,14*a* and right sides 12*b*,14*b* are connected using staples, sutures, surgical adhesive, clips, or other suitable connection means. Alternatively, the studs 22 are non-inflatable, and are frictionally engaged with or adhesively engaged in the corresponding stud-receiving apertures 20. The apertures 20 can be complete apertures or formed as open notches.

Figure 9A:
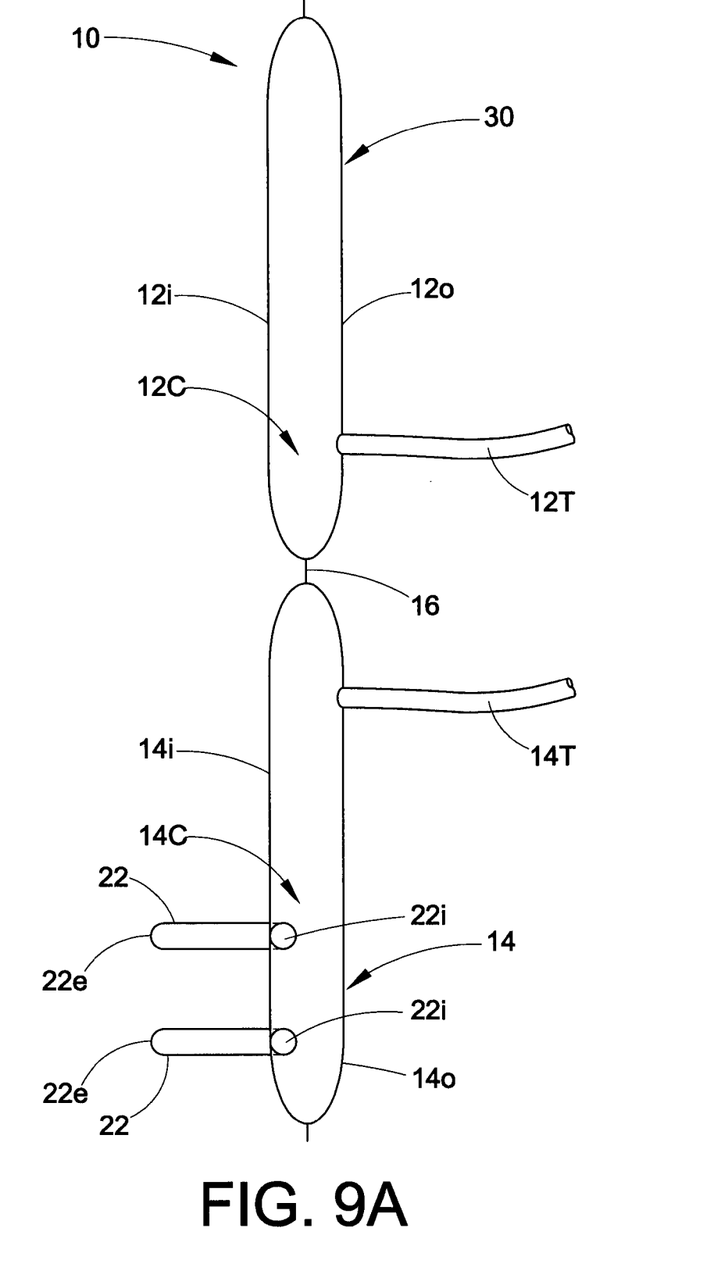
FIG. 9A is a section view as taken at line A-A of FIG. 9.

At least one of the anterior and posterior walls 12,14 of the device 10, or preferably both walls 12,14, include or define an inflatable chamber that is selectively inflated with air or saline or another biocompatible fluid in order to increase the compression force of the device 10 on the uterus U located between the device walls 12,14. As shown herein, the anterior wall 12 comprises an anterior inflation chamber or compartment 12C and the posterior wall comprises a posterior or posterior wall inflation chamber or compartment 14C, and these chambers 12C,14C are fluidically isolated such that each chamber 12C,14C is selectively and independently inflatable with a gas or liquid in order to exert inwardly directed force on the uterus U after the device 10 is operatively installed on the uterus U. In the exemplary embodiment, the chambers 12C and 14C are fluidically isolated from each other, but they can be defined or provided so as to be in fluid communication with each other for simultaneous inflation and deflation. Although the device 10 is shown with only a single inflation chamber 12C,14C in each wall 12,14, multiple separate or fluidically connected inflation chambers can be provided in each wall 12,14. Also, the device can alternatively include only one of the chambers 12C,14C. As shown in FIG. 9A, which is a section view as taken at line A-A of FIG. 9, the anterior device wall 12 comprises inner and outer anterior wall portions 12*i*,12*o*, and the anterior inflation chamber 12C is defined between the inner and outer anterior wall portions 12*i*,12*o*. Likewise, the posterior device wall 14 comprises inner and outer posterior wall portions 14*i*,14*o*, and the posterior inflation chamber 14C is defined between the inner and outer posterior wall portions 14*i*,14*o*.

To inflate and deflate the chambers 12C,14C, the device 10 comprises an anterior inflation conduit 12T that extends through the outer anterior wall portion 12*o* and that is in fluid communication with the anterior inflation chamber 12C, and the device 10 also comprises a posterior inflation conduit 14T that extends through the outer posterior wall portion 14o and that is in fluid communication with the posterior inflation chamber 14C. The liquid or gas used to inflate the chambers 12C,14C is respectively introduced through the conduits 12T, 14T, and the conduits 12T,14T likewise provide a path for liquid or gas to escape from the respective chambers 12C,14C when the chambers 12C,14C are deflated. Of course, if the anterior and posterior inflation chambers 12C,14C are in fluid communication with each other, only one of the inflation conduits 12T,14T is required to inflate and deflate both chambers 12C,14C. The inflation conduits 12T,14T are provided by suitable medical tubing as is generally known in the art. Also, flow of liquid or gas through the conduits 12T,14T is controlled by known clamps, valves, syringes, or like means. A manual or electronic pump can be used to inflate the device 10 to the desired and measurable tension.

As noted above, the fastener studs 22 are selectively inflatable such that they are radially enlarged and frictionally engaged in their respective apertures 20 when inflated, but easily disengaged from in their respective apertures 20 when deflated. In the illustrated embodiment of the device 10, the fastener studs 22 are defined by hollow tubular members that are each closed at the distal end 22e and that each include an inner end 22i that is in fluid communication the inflation chamber 14C (or the inflation chamber 12C if the fastener studs 22 are connected to the anterior wall 12). As such, when the posterior inflation chamber 14C is inflated with liquid or gas, each fastener stud 22 having an inner end 22i in fluid communication therewith is correspondingly inflated and becomes radially enlarged so as to be tightly frictionally engaged in the respective stud-receiving aperture 20 in which it is located. When the chamber 14C is evacuated, each fastener stud 22 is also deflated and naturally resiliently constricts to a reduced diameter or thickness such that it is easily withdrawn from the stud-receiving aperture 20 in which it is received (or easily inserted into one of the stud-receiving apertures 20 during installation).

With particular reference to FIGS. 7-9A, the device 10, comprises a body 30 including the anterior wall 12 and the posterior wall 14. The anterior wall 12 includes the anterior inflation chamber 12C and the posterior wall 14 includes the posterior inflation chamber 14C, each of which chambers 12C,14C is defined between a double-walled portion of the body 30 as described above. In one exemplary embodiment, the body 30 is be defined from a single one-piece molded or otherwise formed polymeric construction. The main joint or seam 16 that separates the anterior wall 12 from the posterior wall 14 is preferably defined by a sealed or crimped or otherwise formed region or web that defines a living hinge or like flexible location where the anterior wall 12 and posterior wall are folded relative to each other. In other embodiments, the main joint or seam 16 is provided by a simple web portion of the body 30, without any crimping or other feature that defines a living hinge, i.e., a simple web of the polymer or other material from which the body 30 is defined provides a flexible hinge-like structure for the main joint 16.

The fastener studs 22 can be defined as part of the one-piece construction that forms the body 30, or the fastener studs 22 can be separately defined and then connected to the body 30. The inflation conduits 12T,14T are shown as being defined separately from but connected to the body 30, but these can also be defined as part of the one-piece construction that forms the body 30. The device further optionally comprises one or more drainage tubes (not shown) secured to the body for draining blood or other fluids from the patient's surgical site.

Figure 10:
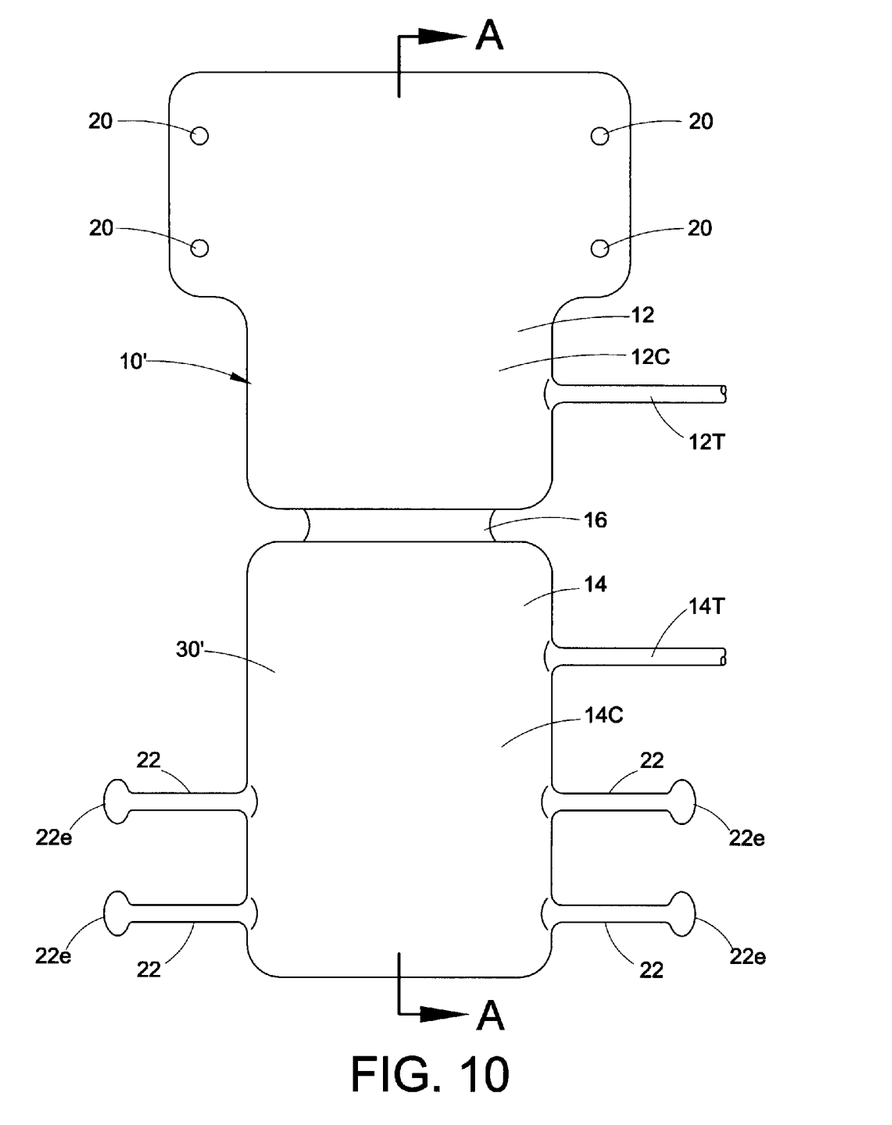
FIG. 10 illustrates an alternative embodiment of a post-partum hemorrhage treatment device 10' which is defined from a one-piece molded or otherwise formed polymeric body.
Figure 10A:
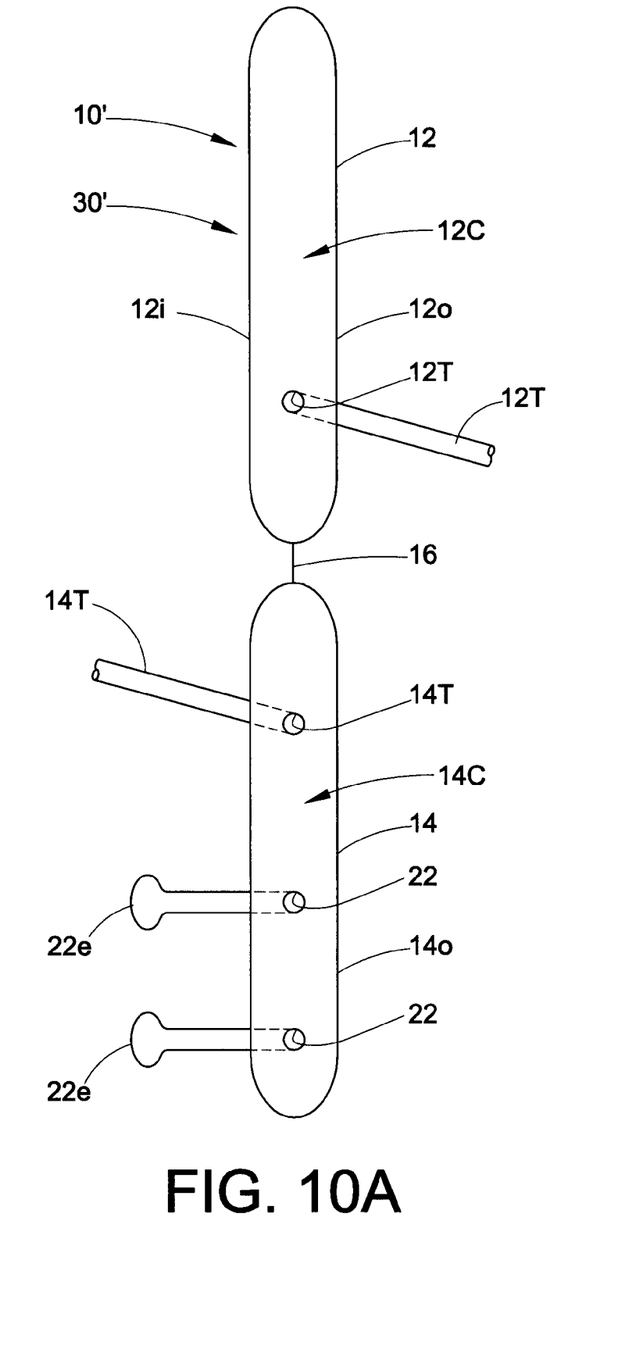
FIG. 10A provides a section view as taken at line A-A of FIG. 10.

FIG. 10 illustrates an alternative embodiment of the device 10' which is otherwise identical to the device 10, except that the device 10' is entirely defined from a one-piece molded or otherwise formed polymeric body 30', including the anterior and posterior walls 12,14, the main joint 16, the anterior and posterior inflation chambers 12C,14C, the stud-receiving apertures 20, the stud fasteners 22, and the anterior and posterior inflation conduits 12T,14T. In this embodiment, the stud fasteners 22 each include an enlarged distal end 22e that is radially enlarged relative to an adjacent portion of the stud fastener and resistant to being pulled through the associated stud-receiving aperture 20 when the stud fastener 22 is inflated. When the stud fastener 22 is deflated, the enlarged distal end 22e is inserted through or withdrawn from the associated stud-receiving aperture during installation or removal of the device 10. FIG. 10A provides a section view as taken at line A-A of FIG. 10.

In use, the device 10 is installed on a uterus U as shown in FIGS. 3-5, and one or both inflation chambers 12C,14C and the stud fasteners 22 are inflated with fluid (liquid and/or gas) such that the chambers 12C,14C press the anterior and posterior walls A,P of the uterus U toward each other to stop the hemorrhage in the uterus. The patient's abdomen containing the device installed on her uterus U is closed such that only the inflation conduits 12T,14T (or the single inflation conduit 12T or 14T if only one is provided) and any drain or other associated features extend from within the patient's abdomen to an external location through a small access incision in the patient's abdomen. When the hemorrhage is stopped, the chambers 12C,14C are deflated through the inflation conduits 12T,14T, and the device 10 is pulled via the inflation conduits 12T,14T from the patient's abdomen through the access incision without having to reopen the patient's abdomen. Those of ordinary skill in the art will recognize that when the chambers 12C,14C are deflated, the stud fasteners 22 are likewise deflated such that they are easily withdrawn from the respective stud-receiving apertures in which they are located. As such, the device 10 can be removed as just described without the necessity of performing another surgical procedure. The intention is to remove the device 24 to 48 hours after insertion.

Other alternative embodiments are possible. The inflation chambers 12C,14C can be omitted, in which case the anterior and posterior walls 12,14 of the device 10 urged toward each other by the stud fasteners 22 or other means in order to urge the anterior and posterior uterine walls into abutment with each other. In another example, the device 10 is constructed with a natural resiliency such that the its anterior and posterior walls 12,14 are normally and continuously resiliently urged toward each other. In such case, the device 10 is installed on a uterus and the natural resiliency of its anterior and posterior walls 12,14 continuously urge the anterior and posterior walls A,P of the uterus U into engagement with each other without requiring any inflation or other activation step.

The anterior and posterior walls 12,14 need not be cover the entire anterior and posterior walls A,P of the uterus U, respectively, and need not even cover a substantial portion of the anterior and posterior uterine walls A,P. It is sufficient that contact between the anterior device wall 12 and anterior uterine wall A and contact between the posterior device wall 14 and the posterior uterine wall P be sufficient that the anterior and posterior uterine walls A,P are urged together to abate uterine bleeding when the device walls 12,14 are connected to each other about the uterus A and the anterior chamber 12C and/or posterior chamber 14C are inflated.

Although the device 10,10' is shown as comprising the anterior and posterior walls 12,14 interconnected through the main joint 16, the anterior and posterior walls 12,14 can be defined as two separate, disconnected structures that are connected to each other only when affixed about the uterus U.

The development has been described with reference to preferred embodiments. Those of ordinary skill in the art will recognize that modifications and alterations to the preferred embodiments are possible. The disclosed preferred embodiments are not intended to limit the scope of the following claims, which are to be construed as broadly as possible, whether literally or according to the doctrine of equivalents.

The invention claimed is:

1. A post-partum hemorrhage treatment device comprising:
   an anterior wall and a posterior wall, each defined from a resilient polymeric material;
   a flexible joint that connects the anterior wall to the posterior wall;
   an anterior inflation chamber located in said anterior wall and a posterior inflation chamber located in said posterior wall, wherein said anterior inflation chamber and said posterior inflation chamber are each adapted for selective inflation;
   at least one inflation conduit in fluid communication with said anterior inflation chamber and said posterior inflation chamber;
   wherein a left lateral side of the anterior wall is adapted to be selectively connected to a left lateral side of the posterior wall, and a right lateral side of the anterior wall is adapted to be selectively connected to a right lateral side of the posterior wall;
   a left stud fastener and a corresponding left stud-receiving aperture both located on a left lateral side of the device, said left stud fastener connected to one of the anterior and posterior walls and said left stud-receiving aperture located in the other of the anterior and posterior walls;
   a right stud fastener and a corresponding right stud-receiving aperture both located on a right lateral side of the device, said right stud fastener connected to one of the anterior and posterior walls and said right stud-receiving aperture located in the other of the anterior and posterior walls;
   said left and right stud fasteners in fluid communication with the respective inflation chamber defined in the wall to which they are respectively connected, wherein said left and right stud fasteners are selectively inflatable hollow tubular members that expand when inflated and are selectively inserted into and retained in the left and right stud-receiving apertures, respectively, to releasably connect said left lateral side of the anterior wall to the left lateral side of the posterior wall, and to releasably connect said right lateral side of the anterior wall to the right lateral side of the posterior wall.

2. The post-partum hemorrhage treatment device as set forth in claim 1, wherein said anterior wall, said posterior wall, and said flexible joint are defined together from a single one-piece polymeric construction.

3. The post-partum hemorrhage treatment device as set forth in claim 1, wherein said at least one inflation conduit comprises:
   an anterior inflation conduit in fluid communication with said anterior inflation chamber; and
   a posterior inflation conduit in fluid communication with said posterior inflation chamber.

4. The post-partum hemorrhage treatment device as set forth in claim 1, wherein said anterior inflation chamber and said posterior inflation chamber are fluidically connected to each other.

5. The post-partum hemorrhage treatment device as set forth in claim 1, wherein said left and right stud fasteners each include an enlarged distal end that is radially enlarged as compared to an adjacent portion of the stud fastener when the fastener stud is inflated.

6. A post-partum hemorrhage treatment device comprising:
   an anterior wall;
   a posterior wall;
   a flexible joint that connects the anterior wall to the posterior wall;
   at least one of the anterior wall and the posterior wall including an inflation chamber that is adapted for selective inflation;
   a left stud fastener and a left stud-receiving aperture both located on a left lateral side of the device;
   a right stud fastener and a right stud-receiving aperture both located on a right lateral side of the device;
   wherein said left stud fastener is connected to one of the anterior and posterior walls and the left stud-receiving aperture is located in the other of the anterior and posterior walls;
   wherein said right stud fastener is connected to one of the anterior and posterior walls and the right stud-receiving aperture is located in the other of the anterior and posterior walls;
   said left and right stud fasteners selectively inserted into and retained in the left and right stud-receiving apertures, respectively, for securing the treatment device relative to a human uterus;
   wherein said left and right stud fasteners are in fluid communication with said inflation chamber and are selectively inflatable hollow tubular members that inflate and expand when said inflation chamber is inflated such that said left and right stud fasteners are frictionally engaged with the left and right stud-receiving apertures in which they are inserted, respectively.

\* \* \* \* \*